United States Patent [19]

Phillips

[11] Patent Number: 4,521,620

[45] Date of Patent: Jun. 4, 1985

[54] ACRYLAMIDE SYNTHESIS FROM AN OIL-IN-WATER EMULSION CONTAINING ACRYLONITRILE

[75] Inventor: Kenneth G. Phillips, River Forest, Ill.

[73] Assignee: Nalco Chemical Company, Oak Brook, Ill.

[21] Appl. No.: 329,010

[22] Filed: Dec. 9, 1981

Related U.S. Application Data

[63] Continuation of Ser. No. 213,279, Dec. 5, 1980, abandoned, which is a continuation of Ser. No. 97,287, Nov. 26, 1979, abandoned.

[51] Int. Cl.[3] .......................................... C07C 102/08
[52] U.S. Cl. .................................... 564/128; 564/126; 564/127
[58] Field of Search ....................... 564/128, 127, 126; 560/240; 260/29.6

[56] References Cited

U.S. PATENT DOCUMENTS

| | | | |
|---|---|---|---|
| 3,284,393 | 11/1966 | Vanderhoff | 260/29.6 |
| 3,624,019 | 11/1971 | Anderson | 260/29.6 |
| 3,920,740 | 11/1976 | Svarz | 564/128 X |
| 3,923,756 | 12/1975 | Svarz | 526/240 |
| 3,997,492 | 12/1976 | Kane | 260/29.6 |

*Primary Examiner*—Robert V. Hines
*Attorney, Agent, or Firm*—John G. Premo; Robert A. Miller; John S. Roberts, Jr.

[57] ABSTRACT

A method of producing acrylamide from acrylonitrile in the presence of a metallic conversion catalyst which comprises contacting an oil-in-water emulsion of acrylonitrile, said water phase being the continuous phase and containing up to 7% acrylonitrile and said oil phase being the dispersed phase and containing the remaining acrylonitrile to be converted to acrylamide, whereby a substantial portion of the acrylonitrile is converted to acrylamide which remains in the aqueous phase of the oil-in-water emulsion, and then an additional low HLB emulsifier is added to invert the oil-in-water emulsion to a water-in-oil emulsion containing acrylamide.

6 Claims, No Drawings

ACRYLAMIDE SYNTHESIS FROM AN OIL-IN-WATER EMULSION CONTAINING ACRYLONITRILE

This is a continuation of application Ser. No. 213,279, filed Dec. 5, 1980, which is a continuation of Ser. No. 097,287 filed Nov. 26, 1979, both now abandoned.

INTRODUCTION

It is now known that acrylamide can be produced by reacting acrylonitrile with water in the presence of a metallic conversion catalyst. These catalytic processes are now being used on a commercial scale. It is common in these processes to react about 7% acrylonitrile dissolved in water in the presence of these metallic catalysts whereby a dilute aqueous solution of acrylamide is produced. These solutions of acrylamide may be polymerized to form water-soluble polymers and copolymers by using a water-in-oil emulsion polymerization technique. This technique is described generally in Vanderhoff U.S. Pat. No. 3,284,393, the disclosure of which is incorporated herein by reference.

The conversion of acrylonitrile to acrylamide as described produces a dilute aqueous solution of acrylamide. These solutions require concentration in order to effectively produce a commercial form of the water-in-oil emulsions which contain the polymers.

If it were possible to prepare relatively concentrated water-in-oil emulsions of acrylamide directly from acrylonitrile, substantial savings would be accomplished. One way to accomplish this goal would be to create an oil-in-water emulsion which contains substantially more acrylonitrile than could be obtained in just an aqueous solution, which normally would contain the 7% acrylonitrile figure previously quoted. I anticipate that the conversion of acrylonitrile to acrylamide from an oil-in-water emulsion containing acrylonitrile could be accomplished when this acrylonitrile containing emulsion is contacted by a metallic conversion catalyst of the type required for this hydrolytic conversion, under the appropriate reaction conditions.

THE INVENTION

This invention describes a method of producing acrylamide from acrylonitrile in the presence of a metallic conversion catalyst which comprises contacting an oil-in-water emulsion of acrylonitrile which contains in both the aqueous phase as well as the dispersed oil phase of this emulsion substantial quantities of acrylonitrile. This oil-in-water emulsion of acrylonitrile being substantially converted to acrylamide in the presence of the metallic conversion catalyst, wherein the oil-in-water emulsion of acrylonitrile either during the conversion to acrylamide or after the conversion to acrylamide is completed has its emulsifier system changed in such a manner as to invert the oil-in-water emulsion product containing acrylamide to a water-in-oil emulsion containing acrylamide. The thus produced water-in-oil emulsion is capable of emulsion polymerization in a manner described in Vanderhoff U.S. Pat. No. 3,284,393.

In a preferred embodiment of the invention the catalyst used is a finely divided metallic copper catalyst having a high degree of activity and, most preferably, a Raney copper catalyst which contains 2-45% by weight of aluminum. In another embodiment of the invention, it is possible to incorporate into the acrylonitrile water-in-oil emulsion sufficient amounts of caustic such as sodium hydroxide or carbonate to convert by hydrolyzing the acrylonitrile or the produced acrylamide to sodium acrylate.

THE METALLIC NITRILE CONVERSION CATALYST

During the last several years, numerous metallic catalysts for converting nitrile and water into amides have been patented or described in the literature. A summary of these catalysts as well as literature references thereto is set forth below:

| Catalyst | Literature Reference |
| --- | --- |
| Raney copper, Ullman copper, reduced copper, copper on a carrier, silver cobalt, nickel, palladium and platinum. | Canadian Patent 899,380 |
| Copper in combination with nickel, chromium manganese, zinc, molybdenum, as well as oxides or sulfides of said metal. | Canadian Patent 930,377 |
| Combinations consisting essentially of 10 to 90% by weight of oxides of copper, silver, zinc or cadmium and 10 to 90% by weight of oxides of chromium or molybdenum. | U.S. Pat. No. 3,597,481 |
| Urushibara - copper chloride precipitate with zinc dust. | Watanabe in Bull. Chem., Soc. Japan, 37.1325 (1964) |
| Copper, copper oxide, copper-chromium oxide, copper-molybdenum oxide or mixtures thereof. | U.S. Pat. No. 3,631,104 |
| Reduced copper oxides in combination with other metal oxides, particularly rare earth metal oxides. | U.S. Pat. No. 3,696,152 |
| Copper prepared by reducing copper hydroxide or a copper salt. | U.S. Pat. No. 3,758,578 |
| Copper metal. | U.S. Pat. No. 3,767,706 |
| Highly active Raney copper. | U.S. Pat. No. 3,920,740 |
| Zinc and cadmium oxides. | German 551,869 |
| Lithium hydroxide. | U.S. Pat. No. 3,686,307 |
| Ruthenium, rhodium, palladium, osmium, iridium or platinum. | U.S. Pat. No. 3,670,021 |
| Fatty acid salts of cadmium, zinc, copper, cobalt, lead, tin, titanium, nickel, iron, mercury; sulfates, nitrates and halides of lead, tin, titanium, nickel, iron, mercury; tin, cadmium & copper oxides; copper powders. | Jap. 70/21,295. Inoue et al., Ashi Kasei Co., 7-18-70. |
| Cupric hydroxide, manganese dioxide, chromium, tungsten, iron or nickel oxide. | Japan 72/33,327 |
| Boron hydroxide & inorganic phosphorous containing acids. | Japan 73/36118 |
| Cobalt chromium catalyst. | Japan 73/39424 |
| Nickel chromium catalyst. | Japan 73/39426 |
| Ruthenium or rhodium. | Japan 73/54,021 |
| Manganese dioxide. | Haefele et al., Ind. Eng. Chem. Prod. Res. Develop. 11(3), 364–365 (1972) |
| Zinc, copper cobalt & cadmium thiocyanates, sulfates, nitrates, halides and cyanides as well as metallic zinc and metallic copper. | Spanish Patent Appl. Public No. 695205 |
| Metal salts of cation exchange resins. | U.S. Pat. No. 3,674,848 |
| Cuprous dihydrogen phosphate. | U.S. Pat. No. 3,679,745 |
| Copper salts. | U.S. Pat. No. 3,381,034 |

Of the above catalysts, I prefer to use in the practice of my invention a special Raney copper catalyst which contains from about 2 to 45% by weight of aluminum. This catalyst in its preferred embodiment contains particles having an average particle diameter ranging from 0.002 to 0.5 inches and has a relative activity of at least about 2. Catalysts of this type as well as their method of preparation are disclosed in U.S. Pat. No. 3,920,740, the disclosure of which is incorporated herein by reference.

As will be shown hereafter, it is important that the metallic catalyst be capable of producing acrylamide from acrylonitrile and water in yields of at least 30% and, preferably, at least 50%. In certain instances, certain of the catalysts listed above are incapable of producing acrylamide in such yields under normal commercial operating conditions. It is understood, therefore, that only those catalysts capable of producing acrylamide in at least a 30% yield are intended to be included in my definition of a metallic conversion catalyst.

THE OIL-IN-WATER EMULSIONS OF ACRYLONITRILE

The components of the emulsions are listed below in terms of their weight percentages:

A. Acrylonitrile:
  1. Generally from 5–60%;
  2. Preferably from 20–40%; and
  3. Most preferably from 25–35%;

B. Water:
  1. Generally from 20–90%;
  2. Preferably from 20–70%; and
  3. Most preferably from 30–55%;

C. Hydrophobic liquid:
  1. Generally from 5–75%;
  2. Preferably from 5–40%; and
  3. Most preferably from 20–30%; and D. Oil-in water emulsifying agent:
  1. Generally from 0.1–21%;
  2. Preferably from 1–15%;
  3. Most preferably from 1.2–10%.

In the above, the general range of acrylonitrile in the oil-in-water emulsion is shown to be 5–60%. This concentration of acrylonitrile can be achieved in the emulsion even though it is only soluble in water up to about 7% by weight. Any of the acrylonitrile above 7% is soluble in the hydrobic liquid phase which when dispersed in the water phase also contains acrylonitrile. It is contemplated that the emulsions can be a dispersion of acrylonitrile in oil emulsified in the water phase at the beginning of the reaction but that the nitrile present would be rapidly converted to acrylamide which would create an acrylamide in water continuous phase which, in turn, would solubilize more of acrylonitrile present in the dispersed oil phase.

It is known that the acrylamide-water solutions tend to form a solvent system for acrylonitrile which allows more than 7% acrylonitrile to be dissolved therein. This is demonstrated below in Table I.

TABLE I

| | Nitrile Solubility |
|---|---|
| Percent by Weight of Acrylamide Solution | Percent by Weight of Nitrile in Solution Based on Water |
| 0 | 7 |
| 10 | 12.99 |
| 20 | 16.0 |
| 40 | 58.66 |
| 50 | 185.6 |
| 60 | 246.0 |

As indicated, in certain instances it is desirable that the acrylonitrile oil-in-water emulsions, in addition to contacting the conversion catalysts, also contained calculated amounts of alkali metal to convert varying amounts of the acrylonitrile and/or acrylamide to sodium acrylate. The alkali also seems to enhance the solubility of the nitrile in the aqueous phase of this oil-in-water emulsion as the conversion of nitrile to amide progresses.

It is also possible to further characterize oil-in-water emulsions which contain acrylonitrile with respect to the continuous aqueous phase of these emulsions. This aqueous phase can generally be defined as some of the acrylonitrile present in the emulsion plus the amount of water. This terminology is somewhat artificial, particularly at the start of the conversion, when the acrylonitrile is predominantly dissolved in the oil phase which is dispersed therein in the continuous water phase. However, it is readily understood that as the conversion of acrylonitrile to acrylamide continues the acrylamide-water-acrylonitrile phase does become predominant, thereby leading to the eventual treatment of the aqueous phase being defined as the sum of the acrylonitrile present in the emulsion plus the amount of water. Utilizing this terminology, the initial aqueous phase of the oil-in-water emulsions of this invention generally consists of 25–95% by weight of the emulsions. Preferably the initial aqueous phase is between 60–90% and, most preferably, from 65–85% by weight of the total oil-in-water emulsion.

The emulsions also may be characterized in relation to the water/oil ratios initially present. This ratio is simply the amount of water present in the emulsion. Generally the oil-in-water emulsions initially present are converted to water-in-oil emulsions which contain acrylonitrile in trace quantities along with the acrylamide/water/oil which would be present as a finished product in the form of a water-in-oil emulsion that has a water/oil ratio of from 0.25–18. Preferably the water/oil ratio will range from 1.0–2.75.

THE HYDROPHOBIC LIQUIDS

The hydrophobic liquids or oils used in preparing these emulsions may be selected from a large group of organic liquids which include liquid hydrocarbons and substituted liquid hydrocarbons.

A preferred group of organic liquids that can be utilized in the practice of this invention are paraffinic hydrocarbons oils. Examples of these types of materials include a branch-chain isoparaffinic solvent sold by Humble Oil and Refinery Company under the tradename "ISOPAR M" described in U.S. Pat. No. 3,624,019, and a paraffinic solvent sold by the Exxon Company, U.S.A. called "Low Odor Paraffinic Solvent." Typical specifications of this material are set forth below in Table II.

TABLE II

| | |
|---|---|
| Specific Gravity 60°/60° F. | 0.780–0.806 |
| Color, Saybolt | +30 min. |
| Appearance, visual | Bright and Clear |
| Aniline Point, °F., ASTM D-611 | 160 min. |
| Distillation, °F., ASTM D-86 | |
| IBP | 365 min. |
| FBP | 505 max. |
| Flash Point, °F., TCC | 140 min. |
| Sulfur, ppm, Microcoulometer | 15 max. |

While paraffinic oils are the preferred materials for use in preparing the water-in-oil emulsions of this invention, other organic liquids can be utilized. Thus, mineral oils, kerosenes, naphthas, and, in certain instances, petroleum may be used. While useful in this invention, solvents such as benezene, xylene, toluene, and other water immiscible hydrocarbons having low flash points or toxic properties are generally avoided due to problems associated with their handling.

THE OIL-IN-WATER EMULSIFYING AGENTS

Any conventional oil-in-water emulsifying agent can be used. Generally speaking nonionic high HLB materials having HLB's from about 11.5 to about 30.5, are preferred. These materials are known to form stable oil-in-water emulsions.

It is preferred to use nonionic materials having HLB's between 13.5 and about 17.0. The use of these intermediate to high HLB materials then allows the addition of relatively small amounts of low HLB emulsifiers to accomplish the inversion of the oil-in-water emulsion to a water-in-oil emulsion which is then capable of polymerization as taught in the Vanderhoff U.S. Pat. No. 3,284,393, the disclosure of which is incorporated herein by reference.

U.S. Pat. No. 3,997,492 shows the use of emulsifiers generally having higher HLB values than normally used to create water-in-oil emulsions which successfully produce stable water-in-oil emulsions. With the use of the equations present in this reference, which is hereinafter incorporated by reference, emulsifier systems having HLB values between 4–9 can be utilized in the formation of the final water-in-oil emulsions which are derived from the initial oil-in-water emulsions of the instant invention.

As indicated, it is possible to conduct a conversion of acrylonitrile or acrylamide in the presence of an alkali such as sodium hydroxide or sodium carbonate which thereby converts a portion of the nitrile or amide groups to sodium acrylate groups. The rate of caustic hydrolysis acrylonitrile to sodium acrylate is described in the work, *The Chemistry of Acrylonitrile,* American Cyanamide Company, 1959, page 11 and 258[1]. For the alkaline hydrolysis of acrylamide, reference should be made to the publication Chemistry of Acrylamide, *American Cyanamid Company,* 1969, page 7. These publications are incorporated herein by reference.
[1]737. Mamiya, J. Soc. Chem. Ind., Japan 44,860 (1941)

The most interesting aspect of this invention is that when the original oil-in-water emulsions of acrylonitrile are prepared using sufficient quantities of an intermediate to high HLB water-in-oil emulsifying agent, the acrylamide produced therefrom by reaction with the previously mentioned catalysts becomes a major component of the continuous aqueous phase of the oil-in-water emulsion. The addition of low HLB water-in-oil emulsifying agents which then lowers the over-all HLB of the system accomplishes an inversion of the original oil-in-water emulsion to create a water-in-oil emulsion containing acrylamide in the dispersed water phase which can be directly utilized in the water-in-oil polymerization system previously described.

CONVERSION CONDITIONS

As a general rule, the conversion of the acrylonitrile to acrylamide may be conducted at temperature ranges from 150°–300° F. with temperatures in the range of 160°–250° being preferred. The preferred catalyst is a Raney copper catalyst of the type described in U.S. Pat. No. 3,920,740, the disclosure of which is incorporated by reference. This patent also shows additional reaction conditions that may be used. While I prefer to use a metallic catalyst such as Raney copper or reduced copper catalyst of the type already described, it is to be understood that homogeneous catalysts, e.g. those which are solbule in water, may be used. Such catalysts would be amine complexes of copper. In such complexes, the copper must be in the zero valence state.

EXAMPLE 1

The process of our invention for converting oil-in-water emulsions of acrylonitrile to water-in-oil emulsions of acrylamide would be expected to function in the following manner:

A. Forming an oil-in-water emulsion which comprises from 20–40% by weight of acrylonitrile, from 20–70% by weight of water, from 5–40% by weight of a hydrophobic liquid, and from 1–16% by weight of an oil-in-water emulsifying agent having a relatively high HLB. These oil-in-water emulsions would be formed by adding the components mentioned above in any order to a vessel which was equipped with a nitrogen blanket, a vigorous agitator, and means for controlling temperature and pressure. After the components have been added, vigorous agitation of the mixture will be anticipated to form the oil-in-water emulsions of the instant invention.

B. Once the above oil-in-water acrylonitrile containing emulsions have been formed, they may be converted to acrylamide in an oil-in-water emulsion by passing said acrylonitrile emulsions formed in the initial step through a catalyst bed which is capable of converting acrylonitrile to acrylamide. Another method which is anticipated is the addition of a preferred catalyst which may accomplish said conversion of acrylonitrile to acrylamide directly into the agitated vessel mentioned above.

C. The original acrylonitrile oil-in-water emulsion formed in Step A above, may then be reacted with the chosen catalyst of Step B at temperatures ranging from 160°–250° F. for a period of time sufficient to accomplish the conversion of acrylonitrile to acrylamide.

It would be expected that emulsions containing 30±5% by weight acrylonitrile, 42.5±7.5 weight percent water, 25±5 weight percent of a hydrophobic liquid, preferably either low odor paraffinic solvent or a branch chained isoparaffinic solvent represented by the trademark ISOPAR M, and 5±3.5% of a high HLB emulsifying agent, preferably having an HLB value between 12 and 30 would be utilized in the formation of a stable oil-in-water emulsion containing acrylonitrile.

This mixture would then be vigorously agitated, protected from oxidizing atmospheres by an inert gas blanket, and either continuously or in a batch manner exposed to a copper based catalyst system, such as the preferred Raney copper catalyst described in U.S. Pat. No. 3,920,740, such exposure to the catalyst being accomplished in a temperature range from 160° F. to 250° F. until which time a substantial portion of the acrylonitrile present in the original water-in-oil emulsions of acrylonitrile is converted to acrylamide.

After the formation of the oil-in-water emulsions of acrylamide, additional surfactants are added up to the limit of total surfactants previously mentioned, in such a manner that the total HLB of the system would be between 4 and 6 and would provide an inversion of the original oil-in-water emulsion to a water-in-oil emulsion containing acrylamide which may then be used in subsequent steps to form polymers.

The resulting product of the above mentioned sequence of reaction steps would be anticipated to be a stable water-in-oil emulsion containing acrylamide and perhaps trace quantities of unconverted acrylonitrile. This final emulsion product could be further treated by the addition of caustic to convert a portion of the acrylamide and/or acrylonitrile to sodium acrylate via a simple hydrolysis reaction. Depending upon how much anionic character a subsequent polymer might be desired to contain, this subsequent caustic addition could be controlled. Following the formation of the stable acrylamide water-in-oil emulsion, it is fully anticipated that the addition of a catalyst system of the free radical type or a catalyst system of the redox free radical type could accomplish the polymerization of this monomer containing emulsion via techniques generally outlined in U.S. Pat. No. 3,284,393, the disclosure of which is incorporated herein by reference. Following the polymerization the products obtained would be expected to be stable water-in-oil emulsions containing polyacrylamide or copolymers derived therefrom containing both neutral amide functionality as well as anionic carboxylic acid functionality.

Having thus described my invention, I claim:

1. A method of producing acrylamide from acrylonitrile in the presence of a metallic conversion catalyst which comprises contacting an oil-in-water emulsion of acrylonitrile, said water phase being the continuous phase and containing up to 7% acrylonitrile and said oil phase being the dispersed phase and containing the remaining acrylonitrile to be converted to acrylamide, with a metallic conversion catalyst, whereby a substantial portion of the acrylonitrile is converted to acrylamide which remains in the aqueous phase of the oil-in-water emulsion, and then an additional low HLB emulsifier is added to invert the oil-in-water emulsion to a water-in-oil emulsion containing acrylamide.

2. The method of claim 1 where the conversion catalyst is a finely divided catalytically species of copper.

3. The method of claim 2 where the finely dispersed conversion catalyst is a Raney copper catalyst which contains from about 2-45% by weight of aluminum.

4. The method of claim 1 where the conversion of acrylonitrile to acrylamide is done in the presence of sufficient sodium hydroxide to convert from 1-50% by weight of the nitrile and/or amide group to sodium acrylate groups.

5. The method of claim 1 where the metallic conversion catalyst is a homogeneous catalyst.

6. The method of claim 1 wherein the low HLB surfactant is added to the oil-in-water emulsion containing acrylamide in sufficient quantities so that the total HLB of the system is between 4 and 12.

* * * * *